US010729391B2

(12) United States Patent
Myyrylainen

(10) Patent No.: US 10,729,391 B2
(45) Date of Patent: Aug. 4, 2020

(54) INTRA-ORAL X-RAY DETECTION

(71) Applicant: Nokia Technologies Oy, Espoo (FI)

(72) Inventor: Lea Myyrylainen, Espoo (FI)

(73) Assignee: Nokia Technologies Oy, Espoo (FI)

( * ) Notice: Subject to any disclaimer, the term of this patent is extended or adjusted under 35 U.S.C. 154(b) by 177 days.

(21) Appl. No.: 15/437,313

(22) Filed: Feb. 20, 2017

(65) Prior Publication Data

US 2017/0238885 A1 Aug. 24, 2017

(30) Foreign Application Priority Data

Feb. 24, 2016 (EP) .................... 16157078.3

(51) Int. Cl.
| | | |
|---|---|---|
| A61B 5/00 | (2006.01) | |
| A61B 6/14 | (2006.01) | |
| A61B 6/00 | (2006.01) | |
| A61B 10/00 | (2006.01) | |
| G01N 33/50 | (2006.01) | |
| A61B 5/145 | (2006.01) | |
| A61B 5/1459 | (2006.01) | |

(52) U.S. Cl.
CPC .............. *A61B 6/145* (2013.01); *A61B 5/00* (2013.01); *A61B 5/1459* (2013.01); *A61B 5/14507* (2013.01); *A61B 5/14546* (2013.01); *A61B 5/682* (2013.01); *A61B 6/4411* (2013.01); *A61B 10/0051* (2013.01); *G01N 33/50* (2013.01)

(58) Field of Classification Search
CPC combination set(s) only.
See application file for complete search history.

(56) References Cited

U.S. PATENT DOCUMENTS

| | | |
|---|---|---|
| 6,256,524 B1 | 7/2001 | Walker et al. |
| 7,563,026 B2 | 7/2009 | Mandelkern et al. |
| 7,613,505 B2 | 11/2009 | Mazuir et al. |
| 8,002,465 B2 | 8/2011 | Ahn |
| 8,898,069 B2 | 11/2014 | Hood et al. |
| 2003/0169847 A1 | 9/2003 | Karellas et al. |
| 2004/0258210 A1 | 12/2004 | Ritter |
| 2005/0226390 A1 | 10/2005 | Ihalainen |
| 2006/0067462 A1* | 3/2006 | Hack ............. A61B 6/145 378/38 |
| 2007/0106138 A1 | 5/2007 | Beiski et al. |
| 2008/0279330 A1 | 11/2008 | Ueki |
| 2009/0047691 A1 | 2/2009 | Huwig et al. |
| 2010/0152599 A1 | 6/2010 | DuHamel et al. |

(Continued)

FOREIGN PATENT DOCUMENTS

| | | |
|---|---|---|
| CN | 1493252 A | 5/2004 |
| CN | 102300979 A | 11/2011 |

(Continued)

OTHER PUBLICATIONS

Office Action received for corresponding European Patent Application No. 16157078.3, dated Aug. 8, 2018, 4 pages.

(Continued)

*Primary Examiner* — Navin Natnithithadha
*Assistant Examiner* — Andrey Shostak
(74) *Attorney, Agent, or Firm* — Alston & Bird LLP

(57) ABSTRACT

An intra-oral system comprising: an x-ray detector configured to detect extra-orally applied x-rays; and a saliva fluid sensing sub-system configured to sense saliva fluid within the oral cavity.

18 Claims, 2 Drawing Sheets

(56) References Cited

U.S. PATENT DOCUMENTS

| | | | | |
|---|---|---|---|---|
| 2010/0291665 A1* | 11/2010 | Margraf | ............... | C07K 17/02 |
| | | | | 435/287.1 |
| 2011/0051903 A1 | 3/2011 | Armencha et al. | | |
| 2011/0054938 A1* | 3/2011 | Hood | ............... | G01N 33/14 |
| | | | | 705/3 |
| 2013/0253286 A1* | 9/2013 | Fridman | ............... | A61B 5/0402 |
| | | | | 600/301 |
| 2014/0212840 A1* | 7/2014 | Nguyen | ............... | A61C 17/043 |
| | | | | 433/92 |
| 2014/0272764 A1 | 9/2014 | Miller | | |
| 2015/0250433 A1 | 9/2015 | Hyde et al. | | |
| 2016/0367188 A1* | 12/2016 | Malik | ............... | A61B 5/682 |
| 2017/0202526 A1* | 7/2017 | Palermo | ............... | A61B 6/04 |
| 2017/0319054 A1 | 11/2017 | Miller et al. | | |

FOREIGN PATENT DOCUMENTS

| | | |
|---|---|---|
| CN | 102711588 A | 10/2012 |
| CN | 104207800 A | 12/2014 |
| CN | 204698735 U | 10/2015 |
| EP | 1477116 A1 | 11/2004 |
| EP | 2392260 A2 | 12/2011 |

OTHER PUBLICATIONS

Extended European Search Report received for corresponding European Patent Application No. 16157078.3, dated Jun. 20, 2016, 6 pages.

Malon et al., "Saliva-Based Biosensors: Noninvasive Monitoring Tool for Clinical Diagnostics", Hindawi BioMed Research International, vol. 2014, 2014, 20 Pages.

Kim et al., "Non-invasive mouthguard biosensor for continuous salivary monitoring of metabolites", The Analyst, vol. 139, No. 7, 2014, pp. 1632-1636.

Hatzistratis et al., "Hybrid Pixel Detectors for Gamma/X-Ray Imaging", Journal of Physics: Conference Series, vol. 637, 2015, pp. 1-4.

"Seeing the Light: Innovative Intraoral Imaging Technologies", Dental Economics, Retrieved on Mar. 21, 2017, VVebpage available at: http://www.dentaleconomics.com/articles/print/volume-105/issue-2/science-tech/seeing-the-light-innovative-intraoral-imaging-technologies.html.

"SOPROLIFE The Blue Revolution", Acteon, Retrieved on Mar. 21, 2017, Webpage available at : https://www.acteongroup.com/en/my-products/imaging/diagnostic-camera/soprolife.

"ScanX DR X-ray Sensor", Allpro Imaging, Retrieved on Mar. 21, 2017, Webpage available at : http://allpro-imaging.aom/vet/scanx-dr-dental-x-ray-sensor-vet.html.

Simon et al., "Transillumination and Reflectance Probes for In Vivo Near-IR Imaging of Dental Caries", Proc Spie Int Sac Opt Eng, vol. 8929, Feb. 18, 2014, pp. 1-16.

"Easy Go CMOS Wireless Intra Oral Camera", Made-in-china.com, Retrieved on Mar. 21, 2017, Webpage available at : http://huaer-technology.en.made-in-china.com/product/mvzxSktIOEVB/China-Easy-Go-CMOS-Wireless-Intra-Oral-3amera.html.

Intraoral Camera & Dental Camera, KAVO Dental Excellence, Retrieved on Mar. 21, 2017, Webpage available at : http://www.kavo.com/en/dental-x-ray-machines-and-diagnostics/intraoral-camera-dental-camera.

"Treatment Planning", Sirona The Dental Company, Retrieved on Mar. 21, 2017, Webpage available at : http://www.sirona.com/en/products/imaging-systems/treatment-planning/?tab=3694.

Extended European Search Report received for corresponding European Patent Application No. 16154968.8, dated Aug. 24, 2016, 4 pages.

Office Action for U.S. Appl. No. 15/426,264, dated Oct. 22, 2018, 9 pages.

Office Action for U.S. Appl. No. 15/426,264, dated Apr. 29, 2019, 9 pages.

Notice of Allowance for U.S. Appl. No. 15/426,264, dated Jul. 17, 2019, 5 pages.

Anastasiou, A. et al., *Biomedical Impact in Implantable Devices-The Transcatheter Aortic Valve As An Example*, BIOMEP 2015, Journal of Physics: Conference Series 637 (2015) 4 pages.

Child, P.L., Jr., *Digital Dentisty: Is This the Future of Dentistry*, Dental Economics [online] [retrieved Feb. 4, 2020]. Retrieved via Internet: https://www.dentaleconomics.com/science-tech/article/16394539/digital-dentistry-is-this-the. . . (Oct. 2011) 13 pages.

CR Systems for Veterinarians // Digital Imaging // ALLPRO Imaging [online] [retrieved Feb. 4, 2016]. Retrieved via the Internet: https://web.archive.org/web/20150826083648/http://allpro-imaging.com/vet/ (Aug. 26, 2015) 3 pages.

Dental Imaging and Diagnosis Tool I SOPROLIFE [online] [retrieved Feb. 4, 2020]. Retrieved via the Internet: https://web.archive.org/web/20161102030130/http://www.soprolife.com/ (Nov. 2, 2016) 1 page.

Clinical Articles of Dental Imaging by Fluorescence I SOPROLIFE [online] [retrieved Feb. 4, 2020]. Retrieved via the Internet: https://web.archive.org/web/20161028105742/http://www.soprolife.com/fluorescence-imaging/clinical-articles.php (Oct. 28, 2016) 2 pages.

Blog by ClearDent Dental Software: software is Key to a Good Digital X-ray [online] [retrieved Feb. 4, 2020]. Retrieved via the Internet: https://web.archive.org/web/20130114071857/http://news.cleardent.com/2013/01/software-is-key-to-good-digital-x-ray.html (Jan. 14, 2013) 5 pages.

Office Action for Chinese Application No. 2017101009878 dated Nov. 12, 2019, 12 pages.

Notice of Allowance for U.S. Appl. No. 15/426,264 dated Feb. 26, 2020.

* cited by examiner

INTRA-ORAL X-RAY DETECTION

TECHNOLOGICAL FIELD

Embodiments of the present invention relate to an intra-oral system and, in particular, an intra-oral system for x-ray detection.

BACKGROUND

An intra-oral x-ray detector may be used to image the bones, teeth and soft tissues within the oral cavity of a human or animal.

Such imagery may be used to identify problems or potential problems such as tooth decay, infection, cancer etc.

BRIEF SUMMARY

According to various, but not necessarily all, embodiments of the invention there is provided an intra-oral system comprising an x-ray detector configured to detect extra-orally applied x-rays; and a saliva fluid sensing sub-system configured to sense saliva fluid within the oral cavity.

According to various, but not necessarily all, embodiments of the invention there is provided a saliva fluid sensor configured to sense saliva fluid within an oral cavity of a subject and configured to be attached to and detached from an intra-oral system comprising an x-ray detector configured to detect extra-orally applied x-rays; and a saliva fluid sensing sub-system comprising a housing for the saliva fluid sensor.

According to various, but not necessarily all, embodiments of the invention there is provided examples as claimed in the appended claims.

BRIEF DESCRIPTION

For a better understanding of various examples that are useful for understanding the brief description, reference will now be made by way of example only to the accompanying drawings in which.

DETAILED DESCRIPTION

Figure 1:
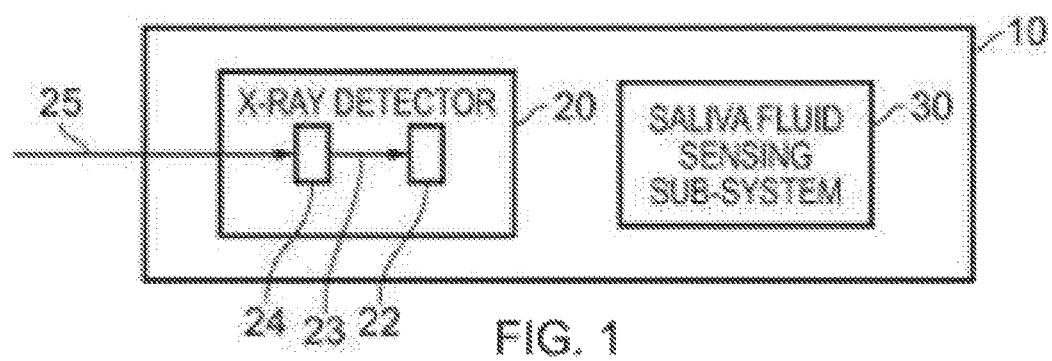
FIG. 1 illustrates an example of an intra-oral system comprising an x-ray detector and a saliva fluid sensing sub-system.

FIG. 1 illustrates an example of an intra-oral system 10 comprising an x-ray detector 20 and a saliva fluid sensing sub-system 30.

The x-ray detector 20 is configured to detect, using at least one or more light sensors 22 light 23 from a scintillator 24. The scintillator 24 is configured to convert extra-orally applied x-rays 25 to the light 23 detected by the one or more light sensors 22.

The x-rays 25 are generated and applied from outside the oral cavity (extra-orally). The x-rays 25, after passing through a target, are converted to lower energy photons using the scintillator 24 and the lower energy photons are detected by the one or more light sensors 22.

The saliva fluid sensing sub-system 30 is configured to enable the sensing of an analyte present in the saliva fluid of a subject. The saliva fluid sensing sub-system 30 is placed within the intra-oral cavity of a subject where saliva is present.

In some, but not necessarily all, examples the saliva fluid sensing sub-system 30 comprises one or more integrated saliva fluid sensors. In other examples, the saliva fluid sensing sub-system 30 comprises one or more housings for receiving and retaining one or more saliva fluid sensors.

A saliva fluid sensor enables the sensing of an analyte or analytes within the saliva fluid of a subject.

In some, but not necessarily all, examples a saliva fluid sensor may be a saliva fluid sampling sensor that samples and retains saliva fluid of the subject. The saliva fluid sampling sensor may then be used to detect and identify an analyte within the saliva fluid.

In some examples, the detection and/or the identification of an analyte may occur in-situ, that is in the in-vivo environment. In other examples, the detection and/or identification may occur ex-situ in an ex-vivo environment. The term 'in-vivo' means that the detection and/or identification of an analyte occur with the saliva fluid sensor(s) 34 positioned within the living subject (e.g. a person or animal). The term 'in-situ' means that the detection and/or identification of an analyte occur with the saliva fluid sensor(s) 34 remaining in its sampling position without the need for it to be removed. The term 'ex-vivo' means that the detection and/or identification of an analyte occurs with the saliva fluid sensor(s) 34 after they have been removed from the living subject (e.g. a person or animal). The term 'ex-situ' means that the detection and/or identification of an analyte occur with the saliva fluid sensing sub-system 30 is removed from its sampling position.

For example, the saliva fluid sampling sensor may, in some examples, be used to physically transport a sample of saliva fluid that is subsequently used to detect and identify an analyte within the saliva fluid. The saliva fluid sampling sensor may, for example, comprise a moisture absorbing pad, which may be mechanically protected to obtain better wear or taste, for example. The saliva fluid sampling sensor may, for example, additionally or alternatively comprise one or more tubes for collecting saliva using the capillary effect. The saliva fluid sampling sensor may, for example, additionally or alternatively comprise one or more pipettes for collecting saliva using a suction effect. The suction effect may for example be created by deformation (squeezing) of the pipette, when a biting block portion is held between a subject's teeth. Alternatively or additionally, the suction effect may for example be created by using an electrically operated micromechanical pump(s).

For example, the saliva fluid sampling sensor may, in some examples, be physically separated from the intra-oral system 100, and be used to physically transport a sample of saliva fluid that is subsequently analyzed at a remote location from the intra-oral system, for example, in a laboratory or elsewhere to identify one or more analytes in the saliva fluid sampled.

In other examples, the saliva fluid sensor may be a saliva fluid detection sensor that is configured to detect one or more analytes within the saliva fluid. In some examples, the saliva fluid detection sensor may communicate information from the intra-oral system relating to the detection of an analyte which can then be used to identify the analyte. In other examples, the detector sensor may be detachable from the intra-oral system to be analyzed at a remote location from the intra-oral system, for example, in a laboratory or elsewhere to identify one or more analytes in the saliva fluid sampled In other examples, the saliva fluid sensor may be a saliva fluid identification sensor that is configured to identify one or more analytes within the saliva fluid. The identification of an analyte requires not only the detection of the presence of analyte but also a classification of the analyte or some other type of identification. In some circumstances where detection of an analyte is analyte specific then a saliva fluid detection sensor also operates as a saliva fluid identification sensor. The saliva fluid identification sensor may be configured to transmit information concerning the identification of an analyte from the intra-oral system. The saliva fluid identification sensor may additionally or alternatively be detachable from the intra-oral system for analysis at a location remote from the intra-oral system, for example, in a laboratory or elsewhere to identify one or more analytes in the saliva fluid sampled.

The saliva fluid sensor may use any one of a number of different technologies to sample the saliva fluid and/or detect one or more analytes in the saliva fluid and/or identify one or more analytes in the saliva fluid.

For example, a saliva fluid sampling sensor may comprise an absorbent material or some other mechanism for trapping saliva fluid.

For example a saliva fluid detection sensor and/or identification sensor may use, for example, a transmitted probe signal to probe the saliva fluid and then receive a response signal. The response signal is related to the probe signal but has been filtered by the saliva fluid. It is therefore possible, for example using signal processing, to extract from the response signal filtering characteristics of the saliva fluid. The filtering characteristics of the saliva fluid may then be used to detect and/or identify analytes within the saliva fluid.

In one example, the probe signal produced by a saliva fluid sensor is an electrical signal that is transmitted through the saliva fluid. The saliva fluid sensor is then able to measure the conductivity of the saliva fluid. This measurement, in some examples in addition to the measurement of temperature, is used to determine a pH measurement of the saliva fluid. A pH measurement is a measurement of the concentration of protons (H+ ions).

In another example, spectroscopy is used by a saliva fluid sensor to analyze the saliva fluid. The transmitted probe signal comprises electromagnetic waves, over a broadband at infrared or near infrared wavelengths. The received response signal comprises the electromagnetic waves filtered by the saliva (an absorption spectra). The absorption peaks and troughs within the spectra obtain may be used to identify analytes within the saliva fluid. In some examples, the spectroscopy is infrared absorption spectroscopy, for example in the sub 3 micrometer wavelength range.

In another example, an antigen responsive hydro gel or other material that is selective to the absorption of particular analytes may be used by a saliva fluid sensor to selectively absorb analytes from the saliva fluid. Such a material may be used within a sampling sensor to retain the analytes or it may be used within a detection and/or identification sensor to, for example, measure the increase in mass or volume of the material using, for example, a piezoresistive cantilever, to detect the presence of the analyte or to identify the analyte.

One example of an anti-gen responsive hydro gel may be prepared by grafting the antigen and corresponding antibody to a polymer network, so that binding between the two introduces crosslinks. Competitive binding of the free antigen triggers a change in gel volume owing to breaking of the crosslinks.

It will therefore be appreciated that there are various technologies and approaches that may be used within a saliva fluid sensor to sample saliva fluid and/or to analyze the saliva fluid for the purpose of detecting and identifying analytes within the saliva fluid whether the detection and/or identification occurs in-situ within the saliva fluid sensing sub-system 30 or occurs elsewhere.

It is therefore possible for the intra-oral system 10 and in particular the saliva fluid sensing sub-system 30 to be used to detect and identify different analytes within saliva fluid including, for example: drugs such as cocaine or its metabolites, glucose, pH, steroid hormones such as cortisol, genetic material such as RNA and DNA, proteins such as, for example enzymes and antibodies, metabolites such as nitrite, hormones associated with ovulation or pregnancy, HIV, cancer, parasites, hypogonadism, allergies, dissolved gases e.g. oxygen, other chemical traces, organic compounds such as acetone or ethanol, non-organic compounds, organophosphates, electrolytes, metals, and/or biomarkers of systemic and local diseases and disorders.

An analyte may, for example, be a marker of endocrine, immunologic, inflammatory, and/or other conditions.

Figure 2:
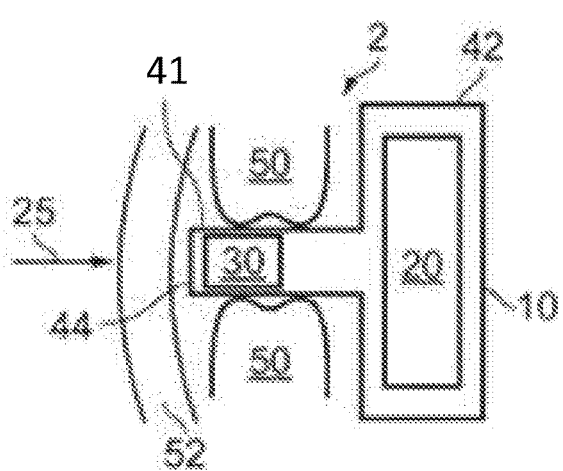
FIG. 2 illustrates an example of the intra-oral system illustrated in FIG. 1 wherein the saliva fluid sensing sub-system is located within a biting block.

FIG. 2 illustrates an example of the intra-oral system 10 described with reference to FIG. 1. In this example, the intra-oral system 10 is positioned within the intra-oral cavity 2. The intra-oral system 10 comprises a biting block portion 41 and an x-ray detector housing portion 42. These two portions are interconnected. The biting block portion 41 is held between the upper teeth and lower teeth 50 by a subject. This positions the biting block portion 41 correctly, which positions the x-ray detector housing portion 42 correctly so that the x-ray detector 20 is correctly positioned within the intra-oral cavity 2. In this example, the x-ray detector 20 is positioned on an anterior side of the teeth 50 of the subject so that the externally applied x-rays 25 pass through the teeth 50 before reaching the x-ray detector 20.

In this example, a portion 44 of the biting block portion 41 is positioned between the cheek and teeth/gums of the subject.

In this example, the biting block portion 41 and, if present, the additional portion 44 may comprise the saliva fluid sensing sub-system 30.

In this example, the biting block portion 41 is large enough to house multiple saliva fluid sensors.

Figure 3:
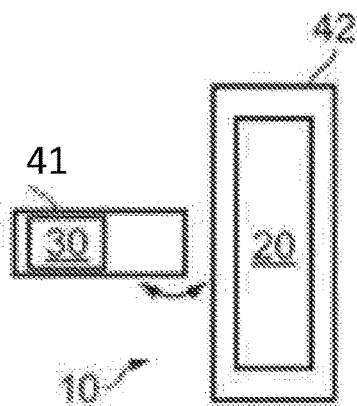
FIG. 3 illustrates the intra-oral system as illustrated in FIG. 2, wherein the biting block is detachable and/or replaceable.

As shown in FIG. 3, the biting block portion 41 may be detached from the x-ray detector housing portion 42. In some but not necessarily all examples the biting block portion 41 may be disposable. In some examples, the biting block portion 41 may be replaced by a replacement biting block portion 41 comprising a different or the same saliva fluid sensing sub-system 30. In this way, the same x-ray detector 20 may be reused with the same or with different patients for the same or different saliva fluid sensing.

The intra-oral system 10 as described may be configured to flex and/or be configured to bend and/or be configured to contort. Likewise, the biting block portion 41 and/or the x-ray detector housing portion 42 may be configured to flex and/or be configured to bend and/or be configured to contort. This may allow the intra-oral system 10 to conform to the intra-oral anatomy of a human or animal. The term "flex" implies that the intra-oral system 10 or a portion of it is pliable and can be acted upon by a user to change its shape. A flexible component may be stably flexible (retains any shape) or may be resiliently flexible (returns to a default shape). The term "bend" implies that the component is configured to change shape so that it has a distinct deviation from a straight line or is a curved bend or angular bend. The term "contort" implies that the component is configured to change its shape so that it is twisted, drawn or bent out of shape.

Figure 4:
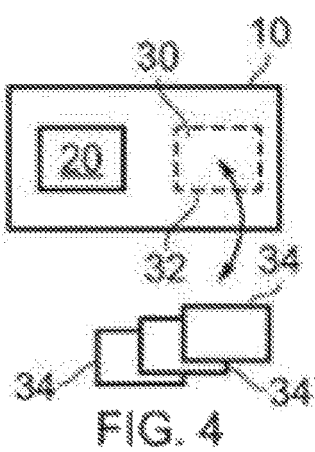
FIG. 4 illustrates an example of the intra-oral system of FIG. 1, wherein the saliva fluid sensing sub-system comprises one or more housings for one or more saliva fluid sensors.

FIG. 4 illustrates an example of the intra-oral system 10 described with reference to any of FIGS. 1-3. In this example, the saliva fluid sensing sub-system 30 provides a housing 32 for the attachment and retention of a saliva fluid sensor 34. In some examples, the saliva fluid sensor 34 once attached to the housing 32 may be subsequently detached and replaced. This may, for example, enable the reuse of the intra-oral system 10 with different saliva fluid sensors 34.

In some examples, there may be multiple different housings 32 each housing a saliva fluid sensor 34 to enable the sensing of multiple different analytes using multiple different saliva fluid sensors 34. In some examples, a single housing may house multiple different saliva fluid sensors 34 to enable the sensing of multiple different analytes using multiple different saliva fluid sensors 34.

FIG. 4 also illustrates a saliva fluid sensor 34 configured to sense saliva fluid within an oral cavity of a subject and configured to be attached to and detached from the intra-oral system 10 comprising an x-ray detector 20 configured to detect extra-orally applied x-rays; and a saliva fluid sensing sub-system 30 comprising a housing 32 for the saliva fluid sensor 34.

Figure 5:
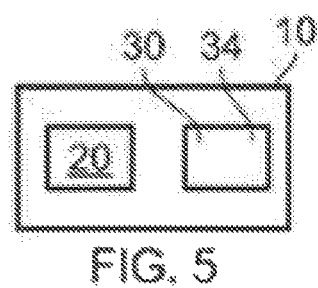
FIG. 5 illustrates an example of the intra-oral system of FIG. 1, wherein the saliva fluid sensing sub-system comprises one or more integrated saliva fluid sensors.

FIG. 5 illustrates an alternative embodiment to that illustrated in FIG. 4. In this example, a saliva fluid sensor 34 is integrated (permanently housed) within the intra-oral system 10.

Figure 6:
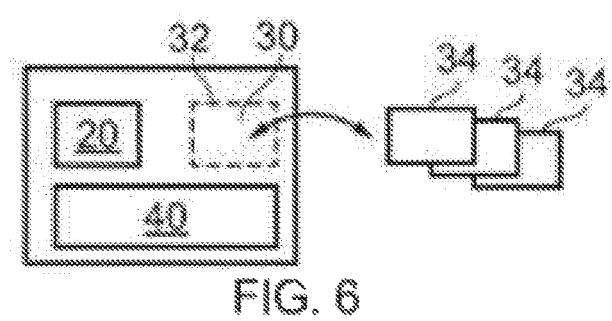
FIG. 6 illustrates an example of the intra-oral system of FIG. 1, wherein the saliva fluid sensing sub-system comprises one or more housings for one or more saliva fluid sensors and comprises common electronic circuitry shared between the x-ray detector and the saliva fluid sensing sub-system.
Figure 7:
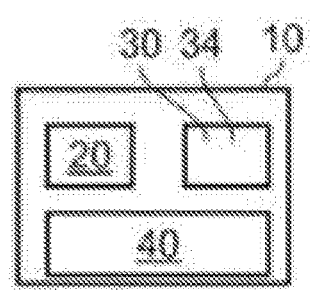
FIG. 7 illustrates an example of the intra-oral system of FIG. 1, wherein the saliva fluid sensing sub-system comprises one or more integrated saliva fluid sensors and comprises common electronic circuitry shared between the x-ray detector and the saliva fluid sensing sub-system.

FIG. 6 illustrates an example of the intra-oral system 10 described with reference to any of FIGS. 1-3. The intra-oral system 10 is similar to that illustrated in FIG. 4, except in this example, the x-ray detector 20 and the saliva fluid sensing sub-system 30 share common electronic circuitry 40. Likewise, FIG. 7 illustrates an intra-oral system 10 similar to that illustrated in FIG. 5 except that the x-ray detector 20 and the saliva fluid sensing sub-system 30 share common electronic circuitry 40.

The shared electronic circuitry 40 may, for example, comprise one or more of: shared signal conditioning circuitry (for amplification and/or filtering and/or analog to digital conversion), shared power management circuitry, shared power source, a shared communication interface for remote communication with another device. The use of shared circuitry reduces volume and cost.

In the examples illustrated, the shared electronic circuitry 40 is housed within the intra-oral system 10. However, in other arrangements, shared electronic circuitry 40 may be external to the intra-oral system 10 and housed in a different device connected wirelessly or otherwise to the intra-oral system 10. This remote system may for example also comprise within the shared electronic circuitry 40 additional circuitry such as for example a display and/or a shared user interface.

Figure 8:
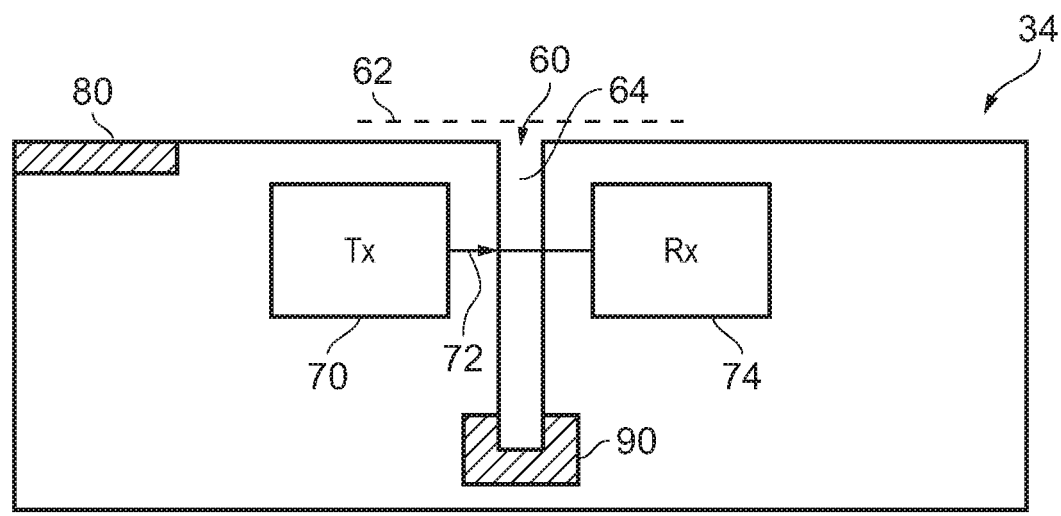
FIG. 8 illustrates an example of a saliva fluid sensor.

FIG. 8 illustrates an example saliva fluid sensor 34 of an intra-oral system 10, for example similar or different to an intra-oral system as described in relation to any of FIGS. 1 to 7.

A saliva fluid sensing sub-system 30 (not shown in FIG. 8) may comprise any number of saliva fluid sensors 34. A saliva fluid sensor 34 may comprise a sensing volume 60. The sensing volume 60 is an isolated volume that samples and retains saliva. In this example, the sensing volume 60 comprises one or more narrow conduits 64 (e.g. tubes) that may, for example, draw in saliva via capillary action.

In other examples, the sampling volume 60 may additionally or alternatively comprise a moisture absorbing pad and/or may additionally or alternatively comprise one or more pipettes for collecting saliva using a suction effect. The suction effect may for example be created by deformation (squeezing) of the pipette, for example, when a biting block portion 41 is held between a subject's teeth. Alternatively or additionally, the suction effect may for example be created by using an electrically operated micromechanical pump(s).

In this example, but not necessarily all examples, the entrance to the conduit 64 comprises a selective medium 62 that filters the saliva before it enters the sensing volume 60. In some examples, the selected medium 62 may not be present.

In this example, the saliva fluid sensor 34 is a detection sensor and/or an identification sensor. It comprises a transmitter 70 that produces a probe signal 72 that passes through the saliva and is received by the receiver 74. The saliva and, in particular the analytes within the saliva, modify the probe signal 72 that is transmitted so that a different modified probe signal is received. The detection of the characteristics of the modified probe signal detects the presence of one or more analytes and the analysis of the characteristics of the detected modified probe signal identifies one or more analytes.

In one example, the saliva fluid sensors 34 may produce as probe signal 72 an electric current and the receiver 74 may measure the conductivity of the saliva. This measurement may, for example, be used to identify the pH of the saliva. In some examples, a temperature sensor may also be required to accurately determine the pH.

In another example, the transmitter 70 may transmit as a probe signal 72 an optical signal such as, for example, infrared light. The presence of the saliva between the transmitter 70 and receiver 74 results in an absorption spectrum being recorded by the receiver 74. This absorption spectrum may be analyzed to detect the presence of particular analytes. For example, infrared absorption spectroscopy may be used to identify a number of different analytes because of their characteristic infrared absorption spectra. In some examples, it may be desirable to filter the transmitted infrared light and/or the received infrared light to limit the range of detection and to assist in the identification of particular analytes.

It will be appreciated that different saliva fluid sensors 34 may include one or more different transmitters and receivers that operate according to one or more different technologies.

In this example, the saliva fluid sensor 34 additionally comprises a physiological response medium 80. This is optional. The purpose of the physiological response medium 80 is to cause a physiological response within the subject to assist in the detection of an analyte. In some examples, the physiological response medium 80 may simply induce the production of saliva. It may for example be a particular flavoring. In other examples it may be designed to illicit a particular physiological response.

In this particular example, there is also illustrated within the saliva fluid sensor 34 a reagent dispenser 90. This is optional. In this example, the reagent dispenser 90 releases a reagent into the sensing volume 60 to mix with saliva fluid. The reagent reacts with a particular analyte in the saliva fluid creating a new substance that is more easily detected by the transmitter 70 and receiver 74 arrangement.

It will therefore be appreciated from the foregoing that the intra-oral system 10 may be used to identify an analyte as previously described with reference to FIG. 1.

Figure 9:
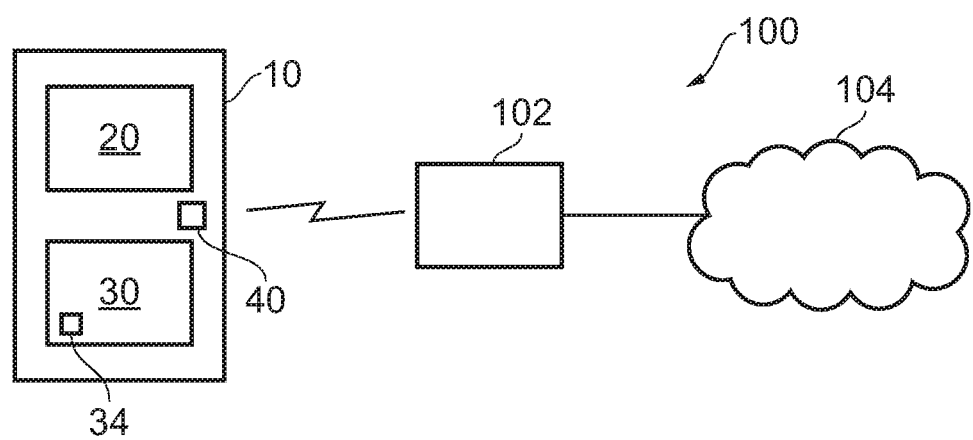
FIG. 9 illustrates an example of a data processing system.

FIG. 9 illustrates an example of a system 100 comprising the intra-oral system 10. In this example, intra-oral system 10 comprises the x-ray detector 20 and the saliva fluid sensing sub-system 30 comprising one or more saliva fluid sensors 34 and shared electronic circuitry 40. In this example, the system comprises a processor 102, which may be part of a local computer, for processing the data recorded by the x-ray detector 20 and the data produced by the one or more of the saliva fluid sensors 34. The processor 102 may be configured to communicate with the shared electronic circuitry 40 of the intra-oral system 10. The processor 102 may be configured to communicate with a remote network 104 such as the internet or "cloud".

In other examples, the system 100 may be configured to communicate with a remote network 104 such as the internet to enable processing of the data recorded by the x-ray detector 20 and/or one or more of the saliva fluid sensors 34.

The method of communication between the various components for example the processor 102 and the x-ray detector 20 and/or the one or more saliva fluid sensors 34 may be via wireless communication such as for example wireless local area network (WLAN) communication.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in the Figs may represent steps in a method. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A system configured to be placed intra-orally, the system comprising:
    an x-ray detector housing comprising an x-ray detector configured to detect extra-orally applied x-rays; and
    at least one biting block,
    wherein the x-ray detector housing further comprises an x-ray detector housing portion configured for attaching thereto the at least one biting block,
    wherein the at least one biting block comprises at least a saliva fluid sensing sub-system comprising at least a saliva fluid sensor,
    wherein when (a) the at least one biting block is attached to the x-ray detector housing portion, and (b) the system is placed intra-orally, the saliva fluid, sensing sub-system is configured to collect saliva fluid,
    wherein the at least one saliva fluid sensing sub-system comprises one or more conduits for collecting and retaining a saliva fluid sample, and
    wherein the one or more conduits are configured for collecting and retaining the saliva fluid sample using a suction effect created when the biting block is held between teeth of a subject and is deformed under an applied biting pressure.

2. The system as claimed in claim 1, wherein the one or more saliva fluid sensors comprise at least one of a saliva fluid sampling sensor for sampling the saliva fluid, a saliva fluid detection sensor for detecting an analyte in the saliva fluid, or a saliva fluid identification sensor for identifying a detected analyte in the saliva fluid.

3. The system as claimed in claim 1, wherein the saliva fluid sensing sub-system is configured for the ex-vivo identification of one or more analytes in the collected saliva fluid sample.

4. The system as claimed in claim 3, wherein the saliva fluid sensing sub-system is detachable from the system.

5. The system as claimed in claim 1, wherein the saliva fluid sensing sub-system is configured for at least one of in-vivo detection or in-vivo identification of one or more analytes.

6. The system as claimed in claim 1, wherein when the at least one biting block is attached to the x-ray detector housing portion, the saliva fluid sensing sub-system shares electronic circuitry with the x-ray detector.

7. The system as claimed in claim 1, wherein the at least one biting block is configured to be held between the teeth of the subject to position the x-ray detector within an intra-oral cavity.

8. The system as claimed in claim 1, wherein when the system is placed intra-orally, the biting block is configured to position one or more light sensors of the x-ray detector adjacent a cheek and a gum of the subject.

9. The system as claimed in claim 1, wherein the x-ray detector comprises a scintillator and one or more light sensors configured to detect light from the scintillator, wherein the scintillator is configured to convert the extra-orally applied x-rays to light for detection by the one or more light sensors when the system is placed intra-orally.

10. The system of claim 1, wherein the saliva fluid sensing sub-system comprises a moisture absorbing pad for collecting the saliva fluid.

11. The system of claim 1, wherein the one or more conduits are configured for collecting and retaining the saliva fluid sample using capillary action.

12. The system of claim 1, wherein the one or more conduits have an entrance comprising a selective medium that filters the saliva.

13. The system of claim 1, wherein the saliva fluid sensor is a detection sensor or an identification sensor that comprises a transmitter that produces a probe signal that passes through the saliva fluid,
    wherein particular analytes within the saliva fluid modify the probe signal that is transmitted so that a different modified probe signal is received by a receiver, and
    wherein detection of the characteristics of the modified probe signal detects the presence of one or more analytes and the analysis of the characteristics of the detected modified probe signal identifies one or more analytes.

14. The system of claim 13, wherein the probe signal comprises an electric current and the receiver measures the conductivity of the saliva fluid, the system further comprising a temperature sensor that measures the temperature of the saliva fluid to identify a pH of the saliva fluid.

15. The system of claim 13, wherein the transmitter transmits, as the probe signal, an optical signal using light;
    wherein light absorption spectroscopy is used to identify different analytes from their characteristic light absorption spectra; and
    wherein a presence of the saliva fluid between the transmitter and receiver results in an absorption spectrum being recorded by the receiver, wherein the absorption spectrum is configured to be analyzed to detect the presence of the analytes.

16. The system of claim 15, wherein the optical signal is filtered to limit a range of detection and to assist in identification of the analytes.

17. A saliva fluid sensing sub-system configured to collect saliva fluid within an oral cavity of a subject, wherein the saliva fluid sensing sub-system is configured in a biting block configured to be attached to and detached from an x-ray detector housing portion of an x-ray detection system configured to be placed intra-orally,
    wherein the x-ray detection system comprises an x-ray detector housing comprising an x-ray detector configured to detect extra-orally applied x-rays,
    wherein the saliva fluid sensing sub-system comprises at least a saliva fluid sensor and one or more conduits for collecting and retaining a saliva fluid sample, and
    wherein the one or more conduits are configured for collecting and retaining the saliva fluid sample using a suction effect created when the biting block is held between teeth of the subject and is deformed under an applied biting pressure.

18. A method comprising:
    collecting saliva fluid with a saliva fluid sensing sub-system configured in at least one biting block that is removably attached to an x-ray detector housing portion of a system configured to be placed intra-orally, wherein the system comprises an x-ray detector housing comprising (a) the x-ray detector housing portion, and (b) an x-ray detector configured to detect extra-orally applied x-rays; and
    detecting a characteristic of the saliva fluid,
    wherein the saliva fluid sensing sub-system comprises at least a saliva fluid sensor and one or more conduits for collecting and retaining a saliva fluid sample, and wherein the one or more conduits are configured for collecting and retaining the saliva fluid sample using a suction effect created when the biting block is held between teeth of a subject and is deformed under an applied biting pressure.

\* \* \* \* \*